US005637561A

United States Patent [19]

Shen et al.

[11] Patent Number: 5,637,561

[45] Date of Patent: Jun. 10, 1997

[54] AGLUCONE ISOFLAVONE ENRICHED VEGETABLE PROTEIN WHEY, WHEY PROTEIN, AND PROCESS FOR PRODUCING

[75] Inventors: Jerome L. Shen, St. Louis; Barbara A. Bryan, University City, both of Mo.

[73] Assignee: Protein Technologies International, Inc., St. Louis, Mo.

[21] Appl. No.: 307,731

[22] PCT Filed: Sep. 21, 1994

[86] PCT No.: PCT/US94/10699

§ 371 Date: Apr. 12, 1996

§ 102(e) Date: Apr. 12, 1996

[87] PCT Pub. No.: WO95/10512

PCT Pub. Date: Apr. 20, 1995

Related U.S. Application Data

[63] Continuation-in-part of Ser. No. 135,192, Oct. 12, 1993, abandoned.

[51] Int. Cl.[6] ........................ A61K 31/335; A61K 38/02; C07K 1/30; C12P 17/06

[52] U.S. Cl. .............................. 514/2; 435/125; 530/370; 530/378; 530/412; 530/414; 530/420; 530/427; 549/403; 514/456

[58] Field of Search .................................... 514/2, 8, 455, 514/456; 435/68.1, 125; 530/343, 370, 377, 378, 407, 412, 414, 419, 420, 427; 549/403

[56] References Cited

U.S. PATENT DOCUMENTS

| | | | |
|---|---|---|---|
| 3,391,001 | 7/1968 | Sair | 426/656 |
| 3,461,205 | 8/1969 | Mansfeld et al. | 530/343 |
| 3,780,182 | 12/1973 | Johnson et al. | 426/33 |
| 3,870,805 | 3/1975 | Hayes et al. | 426/148 |
| 4,064,277 | 12/1977 | Yokotsuka et al. | 426/331 |
| 4,259,358 | 3/1981 | Duthie | 426/46 |
| 4,889,921 | 12/1989 | Diosady et al. | 530/377 |
| 5,320,949 | 6/1994 | Shen | 530/378 |
| 5,352,384 | 10/1994 | Shen | 530/378 |

FOREIGN PATENT DOCUMENTS 258669 10/1989 Japan .

OTHER PUBLICATIONS

Matsuura et al. B–Glucosidases from Soybeans Hydrolyze Daidzin and Genistin. J. Food Science. 1993, vol. 58, No. 1, pp. 144–147.

*Primary Examiner*—Jeffrey E. Russel
*Attorney, Agent, or Firm*—Richard B. Taylor

[57] ABSTRACT

Aglucone isoflavone enriched vegetable protein whey, whey protein and processes for producing and recovering such are disclosed. Aglucone isoflavone enriched vegetable protein whey is made by treating whey comprising glucone isoflavones with a sufficient amount of beta-glucosidase enzyme or esterase enzyme or acid to convert at least a majority of the glucone isoflavones to aglucones and thereby provide an aglucone enriched whey. An aglucone enriched whey protein is obtained by recovery of the protein.

76 Claims, No Drawings

AGLUCONE ISOFLAVONE ENRICHED VEGETABLE PROTEIN WHEY, WHEY PROTEIN, AND PROCESS FOR PRODUCING

This is a continuation-in-part application of U.S. patent application Ser. No. 08/135,192, filed Oct. 12, 1993, now abandoned.

FIELD OF THE INVENTION

The present invention relates to the production of an aglucone isoflavone enriched vegetable protein whey and whey protein, by reacting a vegetable protein whey containing protein and isoflavones with one or more beta-glucosidase enzymes or acid to convert substantially all the glucone isoflavones to aglucones and thereby provide the aglucone enriched whey. An aglucone enriched whey protein is also obtained by recovery of the protein from the enriched whey.

BACKGROUND OF THE INVENTION

Isoflavones occur in a variety of leguminous plants, including vegetable protein materials such as soybeans. These compounds include daidzin, 6-OAc daidzin, 6"-OMal daidzin, daidzein, genistin, 6"-OAc genistin, 6"-OMal genistin, genistein, glycitin, 6"-OAc-glycitin, 6"-OMal-glycitin, glycitein, biochanin A, formononetin and coumestrol. Typically these compounds are associated with the inherent, bitter flavor of soybeans, and in the production of commercial products, such as isolates and concentrates, the focus has been to remove these materials. For example, in a conventional process for the production of a soy protein isolate in which soy flakes are extracted with an aqueous alkaline medium, much of the isoflavones are solubilized in the extract, and remains solubilized in the whey, which is usually discarded following acid precipitation of the protein, to form an isolate. Residual isoflavones left in the acid precipitated protein isolate are usually removed by exhaustive washing of the isolate.

It has been recently recognized that the isoflavones contained in vegetable proteins such as soybeans may inhibit the growth of human cancer cells, such as breast cancer cells and prostate cancer cells as described in the following articles: "Genistein Inhibition of the Growth of Human Breast Cancer Cells, Independence from Estrogen Receptors and the Multi-Drug Resistance Gene" by Peterson and Barnes, *Biochemical and Biophysical Research, Communications*, Vol. 179, No. 1, pp. 661–667, Aug. 30, 1991; "Genistein and Biochanin A Inhibit the Growth of Human Prostate Cancer Cells but not Epidermal Growth Factor Receptor Tyrosine Auto-phosphorylation" by Peterson and Barnes, *The Prostate*, Vol. 22, pp. 335–345 (1993); and "Soybeans Inhibit Mammary Tumors in Models of Breast Cancer" by Barnes, et al. *Mutagens and Carcinogens in the Diet*, pp. 239–253 (1990).

Of the above isoflavones, several exist as glucosides, or as glucones, with a glucose molecule attached at the seven position as illustrated in the formula below. Several of the glucones such as the 6"-OAc genistin, contain an acetate group attached to the six position of the glucose molecule itself. While all the isoflavones, including the glucosides are of interest in medical evaluation, the specific isoflavones of most interest are the aglucones, wherein the glucose molecule is not attached. These isoflavones are not as water soluble as the glucones or glucosides. Specific isoflavones in this category are daidzein, genistein, and glycitein. These aglucones have the following general formula:

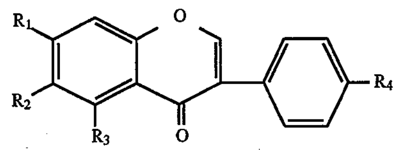

wherein, $R_1$, $R_2$, $R_3$ and $R_4$ may be selected from the group consisting of H, OH and $OCH_3$. It is therefore to the aglucones and enrichment of a vegetable protein whey or whey protein with these materials to which the present invention is directed.

Methods are known in the art for converting glucone isoflavones to aglucone isoflavones, such as described in Japanese Patent Application 258,669 to Obata et al. Such processes achieve only a moderate extent of conversion and so are not desirable, particularly for large scale commercial operations. In addition, known processes such as described in the '669 application teach removing the isoflavones from the protein material and do not describe how to prepare an aglucone isoflavone enriched protein whey. Thus, there is a need for a process of converting at least a majority and preferably substantially all glucone isoflavones to aglucone isoflavones, and for producing an aglucone isoflavone enriched whey and whey protein.

It is therefore an object of the present invention to provide an aglucone isoflavone enriched protein whey, whey protein, and a process for producing the same. This, and other objects, are specifically achieved in the detailed description of the present invention set forth below.

SUMMARY OF THE INVENTION

The present invention provides processes for producing an aglucone isoflavone enriched vegetable protein whey comprising obtaining a vegetable protein whey comprising glucone isoflavones and reacting the glucone isoflavones with a sufficient amount of one or more beta-glucosidase enzymes for a time period, temperature, and pH sufficient to convert at least a majority of the glucose isoflavones in the whey to aglucone isoflavones, and thereby produce an aglucone isoflavone enriched whey. The present invention also provides methods for producing such whey wherein supplemental beta-glucosidase is added to the whey to produce aglucone isoflavone enriched whey. The present invention also provides methods for producing such whey by treatment with one or more acids. In addition, the present invention provides aglucone isoflavone enriched vegetable protein whey and whey products. In addition, the present invention also provides methods of recovering, in relatively high proportions, isoflavones in whey and whey protein, from vegetable protein materials.

DESCRIPTION OF THE PREFERRED EMBODIMENTS

Although the present invention will be described with respect to soybean whey and although the process is particularly suited for the production of aglucone isoflavone enriched whey from soybean materials, nevertheless the process is generally applicable to the production of aglucone enriched wheys from a variety of vegetable protein sources which contain isoflavones. An example of such a source is a vegetable protein material comprising soy or soybean materials. The term "soybean material" as used herein refers to soybeans or any soybean derivative.

The starting material in accordance with the preferred embodiment is soybean flakes, from which the oil has been removed by solvent extraction. The flakes are extracted with an aqueous extractant having a pH above about the isoelectric point of the protein material, preferably a pH of about 6.0 to about 10.0 and most preferably a pH of about 6.7 to about 9.7. Typical alkaline reagents may be employed, if desired to elevate the pH of the aqueous extractant including sodium hydroxide, potassium hydroxide, and calcium hydroxide. The desired isoflavone compounds are typically solubilized in the aqueous extract. It is also desirable, in order to maximize recovery of these compounds in the aqueous extract that the weight ratio of extract to soybean flakes is controlled to specific levels in order to solubilize as much of the inherent isoflavones in the protein material as possible.

Extraction of the proteins and isoflavones can be carried out in a variety of ways including countercurrent extraction of the flakes at a weight ratio of aqueous extractant to flakes of about 8:1 to 16:1, in which the initial extract is used to extract the flakes and provide an aqueous extract of protein and isoflavones. Alternatively, a two-step extraction process can be used in which the weight ratio of extractant to flakes in the initial step comprises about 10:1 and then a second extraction of the flakes with fresh extractant takes place at a weight ratio of extractant to flakes of about 6:1, so that the combined weight ratio of extractant to flakes in both steps does not exceed a total weight ratio of extractant to flakes of about 16:1.

The pH of the resulting protein extract with solubilized isoflavones is then adjusted to about the isoelectric point of the protein in order to precipitate the protein. The pH is adjusted to about the isoelectric point of the protein by the addition of an edible acid such as acetic, sulfuric, phosphoric, hydrochloric or any other suitable reagent. The isoelectric point for soy protein is typically about 4.4 to 4.6. The protein material is precipitated in the form of a curd which can be separated from the aqueous extract. The remaining aqueous extract of the starting material is referred to as the "whey" of whatever vegetable protein source that is used as the starting material. The isoflavones, for the most part remain solubilized in the whey and to maximize recovery in the whey, additional washing of the precipitated protein may be desirable to assure complete recovery of the isoflavones.

Glucone isoflavones in the whey are converted to aglucone isoflavones by reaction with enzyme, or reaction with acid. Conversion utilizing an enzyme is as follows. Glucone isoflavones in whey are reacted in a reaction process, with a sufficient amount of one or more beta-glucosidase enzymes to convert at least a majority, and preferably substantially all isoflavones in glucone form to aglucones. The beta-glucosidase enzyme may be naturally present in the soybean material or present from microbial growth, referred to herein as "residual" enzyme, or may be added to the whey. Added enzyme is referred to herein as "supplemental enzyme". Generally, if the concentration of residual enzyme in the whey is insufficient to convert a majority, and preferably substantially all the isoflavones in glucone form to aglucone form, then supplemental enzyme should be added. The amount of enzyme sufficient to perform the conversion of isoflavones, varies upon a multitude of factors including the types of enzymes present, distribution of enzyme concentrations, pH of the system, and activities of enzymes present. Once sufficient concentrations of enzymes are present, either via residual enzymes, supplemental enzymes, or both, the whey with solubilized isoflavones is reacted with the beta-glucosidase enzymes for a time period, temperature, and pH sufficient to convert at least a majority and preferably substantially all the glucone isoflavones contained in the whey to the aglucone form.

Preferred supplemental beta-glucosidase enzymes include Biopectinase 100L and 300L, Biopectinase OK 70L, Lactase F, and Lactozyme. Lactase F is available from Amano International Enzyme Co, Inc., P.O. Box 1000 Troy, Va. 22974, which has an optimum pH range of about 4 to about 6 and Lactozyme is available from Novo Industries, Enzyme Division, Novo Alle, DK 2880 Bagsvaerd, Denmark which has an optimum pH range of about 7. Biopectinase 100L, Biopectinase 300L, and Biopectinase OK 70L are available from Quest International, Sarasota, Fla. Supplemental enzymes are added in amounts sufficient to convert at least a majority and preferably substantially all the solubilized glucone isoflavones contained in the whey to aglucones. In instances where it is necessary to add supplemental enzymes, the amount of enzyme added is about 0.5% to about 5% by weight of the whey solids on a dry basis.

Another class of enzymes suitable for administration as supplemental enzymes are esterase enzymes. These enzymes are believed to be well suited to the preferred embodiment processes described herein as they convert the acetate and malonate conjugates to glucone isoflavones by removing the acetate and malonate groups from the isoflavone conjugates. In the most preferred embodiment, both types of enzymes, beta-glucosidase and esterase enzymes are utilized.

The processes of the preferred embodiment are preferably one-step processes and achieve very high degrees of conversion of isoflavones (from glucone form to aglucone form), in relatively short periods of time, and with relative ease and economy. The term "one-step" reaction process as used herein refers to a reaction process in which certain process parameter values are generally maintained over the course of the reaction process. These process parameters include pH and temperature.

The very high degrees of conversion are such that at least a majority, and preferably, substantially all the isoflavones in glucone form present in the whey are converted to aglucone form. The term at least "a majority" refers to extent of conversion of glucone isoflavones to aglucone isoflavones of at least about 50%. The term "substantially all" refers to extent of conversion of glucone isoflavones to aglucone isoflavones of at least about 80%, and most preferably at least about 90%.

Although not wishing to be bound to any particular theory, it is believed that the surprisingly and unexpectedly high degrees of conversion of the processes described herein result from a combination of process parameters utilized during the one-step reaction process. It is preferred that pH of the reaction system be maintained, or approximately so, at a value of from about 4 to about 8, and most preferably at a value at which the enzyme(s) are most active prior to reaction with the isoflavone conjugate(s) during the one-step reaction process. The pH of the whey is typically adjusted to about the pH range at which the specific enzyme is most active prior to reaction with the enzyme. It is preferred that the temperature of the reaction system be maintained, or approximately so, at a temperature of from about 40° C. to about 60° C., and most preferably at a temperature of about 60° C. during the one-step reaction process. Generally, the time periods necessary to achieve conversion of substantially all glucone isoflavones to aglucones via the one-step processes described herein are from about 2 hours to about 24 hours. In some instances it may be desirable to utilize time periods greater than 24 hours, such as 48 hours.

An alternative procedure for purposes of the present invention for conversion of glucone isoflavones to aglucone isoflavones, is to react the whey with one or more edible acids at a pH, time, and temperature sufficient to convert at least a majority and substantially all the glucone isoflavones to aglucone isoflavones. This also tends to insolubilize the protein, thereby enabling the protein to be separated from the remaining whey. A preferred pH range for this procedure is from about 1.0 to about 2.0, typical temperatures are from about 80° C. to about 90° C. or higher, and typical time periods are from about 30 to about 180 minutes or longer. The conversion of glucone isoflavones to aglucone isoflavones can also occur at a higher pH. Effective reactions can occur at pH's as high as about pH 4.5. But the reaction is much slower and requires much longer times. For instance, at a pH of 4.5 and temperature of 50° C., a time period of about 24 hours is necessary.

Following conversion of the glucone isoflavones to aglucone isoflavones, the liquid whey may be employed as desired without drying or removal of the protein, or alternatively, the whey protein can be recovered to concentrate the aglucon isoflavones in the protein, since the aglucone isoflavones are less soluble than the glucone isoflavones. Recovery of whey protein enriched with aglucone isoflavones can be accomplished by conventional procedures including dewatering, heat coagulation, and ultrafiltration. The resulting enriched whey protein can be dewatered and dried by conventional means to provide a dried whey protein enriched with aglucone isoflavones. An example of an aglucone isoflavone enriched vegetable whey protein in accordance with the preferred embodiment has a dry basis genistein content of about 2.6 to about 8.7 mg/gram and a dry basis daidzein content of about 2.5 to about 6.0 mg/gram.

The present invention also provides methods of recovering isoflavones in whey and whey protein, in very high proportions, from a vegetable protein material such as a soybean material. The recovery levels obtainable by the processes described herein are typically at least 50%, preferably 65%, and most preferably 80%, based upon the total of all forms of the particular isoflavone in the starting vegetable protein material. Although not wishing to be bound to any particular theory, it is believed that the high recoveries stem from the conversion reactions described herein coupled with the various processing operations also described. By converting glucone isoflavone conjugates, which are relatively soluble, to less soluble aglucone forms, at a particular stage of processing, it is possible to recover in the resulting product, a high percentage of the isoflavones in the feed material.

The following Examples describe specific but non-limiting embodiments of the present invention.

Experimental

Samples of 16% aqueous suspensions of spray dried whey were made in 0.02N phosphate buffer (pH 7) and incubated for 0, 3, and 24 hours at 45° C. with and without added enzyme preparations. The samples receiving supplemental enzyme received Biopectinase 100L in a concentration of 0.4% by weight. All samples were analyzed for isoflavone content. The percent distribution of the isoflavones found over the course of the experiment is indicated in Table 1 set forth below.

TABLE 1

| | | 6"-OMAL- | 6"-OAC- | | | 6"-OMAL- | 6"-OAC- | | | 6"-OMAL- | |
|---|---|---|---|---|---|---|---|---|---|---|---|
| SAMPLE | GENISTIN % | GENISTIN % | GENISTIN % | GENISTEIN % | DAIDZIN % | DAIDZIN % | DAIDZIN % | DAIDZEIN % | GLYCITIN % | GLYCITIN % | GLYCITEIN % |
| No Added Enzyme | | | | | | | | | | | |
| t = 0 | 46 | 44 | 1 | 9 | 47 | 44 | 3 | 5 | 48 | 38 | 14 |
| t = 3 | 51 | 40 | 0 | 8 | 48 | 44 | 3 | 6 | 50 | 32 | 18 |
| t = 24 | 54 | 36 | 0 | 10 | 54 | 38 | 2 | 6 | 60 | 33 | 8 |
| +Biocon Biopectinase 100 L | | | | | | | | | | | |
| t = 3 | 48 | 38 | 0 | 14 | 44 | 43 | 1 | 12 | 55 | 33 | 13 |
| t = 24 | 19 | 12 | 0 | 70 | 15 | 15 | 4 | 66 | 55 | 21 | 24 |

aglucone isoflavone concentration of samples in which no enzyme was added, after 24 hours incubation, was relatively low, e.g. genistein 10%, daidzein 6%, and glycitein 8%. The beneficial effect of the addition of supplemental enzyme is demonstrated by the significantly higher concentrations of genistein and daidzein, e.g. 70% and 66%, respectively. The concentration of each type of isoflavone described herein is based upon the total of all forms of that isoflavone type.

In another experiment, samples of whey were adjusted to pH 7. Samples were incubated at 45° C. After 24 hours incubation, in one-half of the samples, sufficient amounts of a supplemental beta-glucosidase enzyme was added, Biopectinase 100L. All samples were placed at 45° C. and incubated an additional 22 hours. Subsamples were taken at t=0, 5, 24, and 46 hours and analyzed. All samples were analyzed for isoflavone content. The percent of each isoflavone found over the course of the experiment is indicated in Tables 2A and 2B set forth below. Table 2A summarizes the isoflavone content of samples in which no supplemental beta-glucosidase enzyme was added. Table 2B indicates the isoflavone distribution in samples that had originally been incubated 24 hours without having any supplemental enzyme added, which then received a sufficient amount of Biopectinase 100L. Thus, the times indicated in Table 2B are with respect to the event of adding supplemental enzyme to the samples. For instance, the samples indicated for t=0 hours in Table 2B were actually incubated for 24 hours without any enzyme. And the samples listed in Table 2B at t=22 hours, were incubated for 22 hours subsequent to the addition of the supplemental enzyme and incubated for 24 hours prior to the addition of supplemental enzyme.

TABLE 2A

| Sample | 6"-OMal- 6"-OAc- | | | | 6"-OMal- 6"-OAc- | | | | 6"-OMal- | | |
|---|---|---|---|---|---|---|---|---|---|---|---|
| | Genistin % | Genistin % | Genistin % | Genistein % | Daidzin % | Daidzin % | Daidzin % | Daidzein % | Glycitin % | Glycitin % | Glycitein % |
| 1° Whey, pH 7, 45° C. No Added Enzyme | | | | | | | | | | | |
| t = 0 | 11 | 70 | 0 | 19 | 9 | 71 | 0 | 19 | 27 | 63 | 10 |
| t = 5 hrs | 5 | 67 | 0 | 27 | 4 | 69 | 0 | 27 | 0 | 72 | 29 |
| t = 24 hrs | 11 | 58 | 0 | 31 | 9 | 59 | 0 | 32 | 0 | 66 | 34 |
| t = 46 hrs | 8 | 48 | 0 | 45 | 8 | 50 | 0 | 42 | 0 | 57 | 43 |

TABLE 2B

| Sample | 6"-OMal- 6"-OAc- | | | | 6"-OMal- 6"-OAc- | | | | 6"-OMal- | | |
|---|---|---|---|---|---|---|---|---|---|---|---|
| | Genistin % | Genistin % | Genistin % | Genistein % | Daidzin % | Daidzin % | Daidzin % | Daidzein % | Glycitin % | Glycitin % | Glycitein % |
| 1° Whey, pH 7, 45° C. Added Biopectinase 100 L Usage: 0.2 g per 100 g whey | | | | | | | | | | | |
| t = 0 hrs | 11 | 58 | 0 | 31 | 9 | 59 | 0 | 32 | 0 | 66 | 34 |
| t = 22 hrs | 0 | 0 | 0 | 100 | 0 | 0 | 0 | 100 | 0 | 14 | 87 |

The data in Table 2A illustrate samples having marginally sufficient residual enzyme concentrations since the genistein, daidzein, and glycitein concentrations, after incubation for 24 and 46 hours are less than 50%. The data in Table 2B illustrate the benefits of adding supplemental enzyme, since after addition of the enzyme, conversion was 100% for genistein and daidzein and 87% for glycitein.

In another series of experiments, samples of whey were adjusted to a pH of 4.5 and incubated with supplemental enzyme Lactase F. The concentration of Lactase F was 0.02 gram Lactase F per 100 grams whey. Samples were taken at t=0, 1.5, 5, and 17 hours during incubation at 52° C. Table 3 shows the change and distribution of the isoflavones over the course of the experiment.

The data in Table 3 illustrate significant conversion to glycitein after 17 hours.

In another experiment, samples of whey were autoclaved to destroy residual enzymes and contaminate microbes, pH adjusted to 4.5, the samples split into two groups and enzyme added as follows. To the first group of samples, 0.1 gram of supplemental enzyme preparation was added per each 100 grams primary whey in the samples. To the second group, 0.001 gram of supplemental enzyme preparation was added per each 100 grams of whey (enzyme was diluted 1 to 100 for this use). Whey samples were incubated at either 40° C. or 60° C. for 23 hours. Subsamples were withdrawn at t=0, 1, 2, 4, 6, and 23 hours. The supplemental enzyme Biopectinase 300L, was provided by Quest International. All

TABLE 3

| Sample | 6"-OMal- 6"-OAc- | | | | 6"-OMal- 6"-OAc- | | | | 6"-OMal- | | |
|---|---|---|---|---|---|---|---|---|---|---|---|
| | Genistin % | Genistin % | Genistin % | Genistein % | Daidzin % | Daidzin % | Daidzin % | Daidzein % | Glycitin % | Glycitin % | Glycitein % |
| °Whey, pH 4.5, 52° C. Added Lactase F (Amano) Usage: 0.02 g per 100 g whey) | | | | | | | | | | | |
| t = 0 | 11.6 | 68.8 | 0 | 19.6 | 19.5 | 71.2 | 0 | 19.3 | 15.1 | 75.2 | 9.7 |
| t = 1.5 hrs | 9.9 | 64.1 | 0 | 26.0 | 7.0 | 68.2 | 0 | 24.8 | 0 | 57.3 | 42.7 |
| t = 5.0 hrs | 6.5 | 74.1 | 0 | 19.4 | 7.7 | 63.8 | 0 | 28.5 | 0 | 53.0 | 47.0 |
| t = 17 hrs | 9.0 | 47.8 | 0 | 43.2 | 7.3 | 52.4 | 0 | 40.3 | 0 | 42.5 | 57.5 |

samples were analyzed for isoflavone content. The distribution of the isoflavones found over the course of the experiment is set forth below in Table 4. Biopectinase 300L converted isoflavone conjugates to aglucones to 90% genistein, 86% daidzein, and 60% glycitein at pH 4.5, 60° C., after 23 hours using 0.1 gram enzyme preparation per 100 grams whey. Considerable conversion had occurred after only 1 hour at 60° C. with Biopectinase 300L, as demonstrated by 70% genistein, 62% daidzein, and 44% glycitein. The conversion rate and the dose level of 0.1 gram enzyme preparation per 100 grams whey was effective at both 40° C. and at 60° C. The supplemental enzyme dose rate of 100 times more dilute (0.001 grams per 100 grams primary whey) was not 100 times slower.

TABLE 4

| | | 6"-OMAL- | 6"-OAC- | | | 6"-OMAL- | 6"-OAC- | | | 6"-OMAL- | |
|---|---|---|---|---|---|---|---|---|---|---|---|
| SAMPLE | GENISTIN % | GENISTIN % | GENISTIN % | GENISTEIN % | DAIDZIN % | DAIDZIN % | DAIDZIN % | DAIDZEIN % | GLYCITIN % | GLYCITIN % | GLYCITEIN % |
| 0.1 g Biopectinase 300 L, 40 C. | | | | | | | | | | | |
| t = 0 hrs | 45 | 28 | 0 | 27 | 45 | 27 | 6 | 22 | 40 | 28 | 33 |
| t = 1 hr | 23 | 26 | 0 | 51 | 22 | 27 | 5 | 46 | 37 | 27 | 37 |
| t = 2 hrs | 14 | 25 | 0 | 61 | 14 | 26 | 5 | 55 | 36 | 26 | 38 |
| t = 4 hrs | 8 | 22 | 0 | 70 | 9 | 24 | 4 | 64 | 37 | 23 | 40 |
| t = 6 hrs | 6 | 19 | 0 | 74 | 9 | 21 | 3 | 68 | 37 | 22 | 42 |
| t = 23 hrs | 4 | 6 | 0 | 90 | 6 | 8 | 0 | 86 | 34 | 15 | 51 |
| 0.1 g Biopectinase 300 L, 60 C. | | | | | | | | | | | |
| t = 0 hrs | 45 | 28 | 0 | 27 | 45 | 27 | 6 | 22 | 40 | 28 | 33 |
| t = 1 hr | 7 | 24 | 0 | 70 | 9 | 25 | 4 | 62 | 32 | 24 | 44 |
| t = 2 hrs | 5 | 20 | 0 | 74 | 6 | 22 | 3 | 68 | 34 | 22 | 44 |
| t = 4 hrs | 5 | 15 | 0 | 80 | 8 | 17 | 2 | 73 | 32 | 18 | 51 |
| t = 6 hrs | 5 | 11 | 0 | 83 | 9 | 14 | 0 | 77 | 30 | 17 | 53 |
| t = 23 hrs | 8 | 3 | 0 | 90 | 10 | 4 | 0 | 86 | 31 | 8 | 60 |
| 0.001 g Biopectinase 300 L, 40 C. | | | | | | | | | | | |
| t = 0 hrs | 45 | 28 | 0 | 27 | 45 | 27 | 6 | 22 | 40 | 28 | 33 |
| t = 1 hr | 41 | 27 | 0 | 32 | 40 | 27 | 6 | 27 | 36 | 29 | 35 |
| t = 2 hrs | 40 | 26 | 0 | 34 | 38 | 27 | 6 | 29 | 40 | 27 | 33 |
| t = 4 hrs | 35 | 27 | 0 | 38 | 33 | 27 | 6 | 34 | 41 | 26 | 33 |
| t = 6 hrs | 31 | 23 | 0 | 45 | 28 | 24 | 6 | 41 | 39 | 25 | 37 |
| t = 23 hrs | 14 | 21 | 0 | 65 | 12 | 22 | 5 | 62 | 41 | 20 | 39 |
| 0.001 g Biopectinase 300 L, 60 C. | | | | | | | | | | | |
| t = 0 hrs | 45 | 28 | 0 | 27 | 45 | 27 | 6 | 22 | 40 | 28 | 33 |
| t = 1 hr | 34 | 27 | 0 | 40 | 34 | 27 | 6 | 34 | 41 | 26 | 33 |
| t = 2 hrs | 29 | 25 | 0 | 46 | 28 | 26 | 6 | 40 | 38 | 26 | 36 |
| t = 4 hrs | 24 | 24 | 0 | 52 | 24 | 24 | 6 | 46 | 39 | 24 | 37 |
| t = 6 hrs | 24 | 20 | 0 | 56 | 23 | 21 | 6 | 50 | 40 | 21 | 38 |
| t = 23 hrs | 31 | 12 | 0 | 57 | 30 | 13 | 5 | 53 | 47 | 13 | 40 |

The data in Table 4 illustrate the significant extent of conversion that is attainable by the processes of the present invention.

In another series of experiments, samples of whey were pH adjusted to 7 and to 8, and 0.05 gram Lactase F or Lactozyme was added per 5 grams primary whey (5% enzyme by weight of estimated 2% solids in the primary whey). Samples were incubated at 40° C. and at 60° C. A sample was withdrawn before enzyme was added (t=0) and after 24 hours incubation at target temperatures. The enzyme preparation was made as follows. Controls were samples incubated without added enzymes. All samples were analyzed for isoflavone content. The change in percent distribution of isoflavone in whey after the 24 hour incubation period with either Lactase F or Lactozyme is shown in Table 5 set forth below. The samples were not sterilized before adding enzymes in microbial contaminant growth was not inhibited in any way.

TABLE 5

| SAMPLE | GENISTIN % | 6"-OMAL-GENISTIN % | 6"-OAC-GENISTIN % | GENISTEIN % | DAIDZIN % | 6"-OMAL-DAIDZIN % | 6"-OAC-DAIDZIN % | DAIDZEIN % | GLYCITIN % | 6"-OMAL-GLYCITIN % | GLYCITEIN % |
|---|---|---|---|---|---|---|---|---|---|---|---|
| t = 0 | 10 | 63 | 0 | 27 | 10 | 66 | 1 | 23 | 9 | 50 | 41 |
| pH 7.0, 40 C., t = 24 hrs | | | | | | | | | | | |
| no added enzyme | 10 | 46 | 0 | 44 | 10 | 51 | 0 | 39 | 6 | 42 | 52 |
| Lactase F | 5 | 36 | 0 | 60 | 6 | 43 | 0 | 50 | 0 | 31 | 69 |
| Lactozyme | 8 | 52 | 0 | 40 | 8 | 57 | 0 | 35 | 0 | 44 | 56 |
| pH 7.0, 60 C., t = 24 hrs | | | | | | | | | | | |
| no added enzyme | 4 | 18 | 0 | 78 | 6 | 28 | 0 | 66 | 0 | 18 | 82 |
| Lactase F | 11 | 24 | 0 | 65 | 14 | 30 | 0 | 56 | 9 | 20 | 71 |
| Lactozyme | 3 | 17 | 0 | 79 | 5 | 26 | 0 | 69 | 0 | 17 | 83 |
| pH 8.0, 40 C., t = 24 hrs | | | | | | | | | | | |
| no added enzyme | 9 | 48 | 0 | 43 | 8 | 53 | 0 | 39 | 8 | 25 | 67 |
| Lactase F | 7 | 42 | 0 | 51 | 7 | 49 | 0 | 44 | 0 | 10 | 90 |
| Lactozyme | 9 | 49 | 0 | 42 | 8 | 54 | 0 | 38 | 0 | 42 | 58 |
| pH 8.0, 60 C., t = 24 hrs | | | | | | | | | | | |
| no added enzyme | 2 | 8 | 0 | 90 | 4 | 20 | 0 | 76 | 0 | 11 | 89 |
| Lactase F | 9 | 22 | 0 | 69 | 11 | 28 | 0 | 61 | 9 | 19 | 73 |
| Lactozyme | 0 | 7 | 0 | 93 | 3 | 14 | 0 | 84 | 0 | 7 | 93 |

Referring to Table 5, an increase in conversion to genistein of 40% to 79% occurred at pH of 7 and after 24 hours of incubation by increasing incubation temperature from 40° C. to 60° C. Similarly, even greater conversions can be performed by increasing pH, such as from 7 to 8. With respect to genistein, conversion increased from 79% to 93% by that pH change at a temperature of 60° C. and time of 24 hours.

In another series of experiments, the percent recovery of genistein and daidzein in a whey protein derived from soybeans was investigated. The percent recovery was found by determining the amount of genistein (or daidzein) in the whey protein, and expressing that amount as a percentage based upon the total amount of all forms of genistein (or daidzein) in the soybean starting material. 100 g of defatted soy flour was extracted with 1000 g of water at 32° C. for 15 minutes. The pH of the slurry was 6.7. This provided a ratio of extractant to flour of 10.1. The slurry was then centrifuged for 5 minutes to remove the spent flour. The spent flour was extracted a second time with 600 grams of water at 32° C. for 5 minutes. This provided a ratio of extractant to flour of 6:1. The second extract was also separated from the spent flour by centrifugation for 5 minutes. The first and second aqueous extracts were combined. The combined extracts were adjusted to a pH of 4.5 by the addition of HCl to precipitate the protein from the soy whey. The soy whey was spray dried and then resuspended in water to a 20% solids level. The pH of the whey slurry was adjusted to 4.5 and the temperature maintained at 50° C. One percent by weight of the whey solids of Lactase F, an enzyme having beta-glucosidase activity, was added and allowed to react for 20 hours at 50° C. to ensure complete conversion of the glucone isoflavones to the aglucone form. Following reaction, the whey slurry was heated to 95° C. for one minute in order to insolubilize the whey proteins. The insoluble whey protein containing the aglucone isoflavones was recovered by centrifugation. The amount of genistein recovered in the whey protein was 81% of the total of all forms of genistin and genistein in the starting soybean material (defatted soy flour). Similarly, the amount of daidzein recovered in the whey protein was 69%.

The isoflavone content was quantified as follows. The isoflavones are extracted from soy products by mixing 0.75 g of sample (spray dried or finely ground powder) with 50 ml of 80/20 methanol/water solvent. The mixture is shaken for 2 hours at room temperature with an orbital shaker. After 2 hours, the remaining undissolved materials are removed by filtration though Whatman No. 42 filter paper. Five ml of the filtrate are diluted with 4 ml of water and 1 ml of methanol.

The extracted isoflavones are separated by HPLC (High Performance Liquid Chromatography) using a Beckman C18 reverse phase column. The isoflavones are injected on to the column and eluted with a solvent gradient starting with 88% methanol, 10% water, and 2% glacial acetic and ending with 98% methanol and 2% glacial acetic. At a flow rate of 0.4 ml/min, all the isoflavones—genistin, 6"-0-Acetylgenistin, 6"-0-Malonylgenistin, genistein, daidzin, 6"-0-Acetyldaidzin, 6"-0-Malonyldaidzin, daidzin, glycitin and its derivatives and glycitein—are clearly resolved. Peak detection is by UV absorbance at 262 mm. Identification of the peaks was by mass spectrometer.

Quantification is achieved by using pure standards (genistin, genistein, daidzin and daidzein) purchased from Indofine Chemical Company, Sommerville, N.J. Response factors (Integrated area/concentration) are calculated for each of the above compounds and are used to quantitate unknown samples. For the conjugated forms for which no pure standards are available, response factors are assumed to be that of the parent molecule but corrected for molecular weight difference. The response factor for glycitin is assumed to be that for genistin corrected for molecular weight difference.

This method provides the quantities of each individual isoflavone. For convenience, total genistein, total daidzein and total glycitein can be calculated and represent the aggregate weight of these compounds if all the conjugated forms are converted to their respective unconjugated forms. These totals can also be measured directly by a method using acid hydrolysis to convert the conjugated forms.

Of course, it is understood that the foregoing are merely preferred embodiments of the invention and that various changes and alterations can be made without departing from the spirit and broader aspects thereof as set forth in the appended claims, which are to be interpreted in accordance with the principals of patent law including the Doctrine of Equivalents.

The embodiments of the invention in which an exclusive property or privilege is claimed are defined as follows:

1. A process for producing an aglucone isoflavone enriched vegetable protein whey comprising:

(a) obtaining a vegetable protein whey comprising glucone isoflavones; and (b) reacting said glucone isoflavones with a sufficient amount of at least one beta-glucosidase enzyme and esterase enzyme for a time period, temperature, and pH sufficient to convert at least a majority of said glucone isoflavones in said whey to aglucone isoflavones, and thereby produce an aglucone isoflavone enriched whey.

2. The process as set forth in claim 1 wherein said time period is from about 2 hours to about 48 hours.

3. The process as set forth in claim 2 wherein said time period is about 24 hours.

4. The process as set forth in claim 1 wherein said temperature is about 40° C. to about 60° C.

5. The process as set forth in claim 4 wherein said temperature is about 60° C.

6. The process as set forth in claim 1 wherein said pH is from about 4 to about 8.

7. The process as set forth in claim 6 wherein said pH is about 4.5.

8. The process as set forth in claim 1 wherein said time period is about 24 hours, said temperature is about 60° C., and said pH is about 4.5.

9. The process as set forth in claim 1 further comprising:

(c) recovering a protein material from said whey to provide an aglucone isoflavone enriched whey protein.

10. The process as set forth in claim 9 wherein said whey protein comprises soybean whey.

11. The process as set forth in claim 9 wherein said whey protein is recovered by at least one of ultrafiltration, heat coagulation, and dewatering.

12. The process as set forth in claim 9 wherein said whey protein is recovered by a process which comprises heating said whey at a pH, time and temperature sufficient to insolubilize said protein and thereafter separating said insolubilized protein from said whey.

13. The process as set forth in claim 12 wherein said pH is about 1 to about 2.

14. The process as set forth in claim 12 wherein said temperature is at least about 80° C. for at least about 30 minutes.

15. The process as set forth in claim 12 wherein said insolubilized protein is separated from said whey by centrifugation.

16. The process as set forth in claim 12 wherein said insolubilized protein is dewatered.

17. The aglucone isoflavone enriched whey produced from the process as set forth in claim 1.

18. The aglucone isoflavone enriched whey protein produced from the process as set forth in claim 9.

19. The process as set forth in claim 1 wherein substantially all glucone isoflavones are converted to aglucone isoflavones.

20. A process for producing an aglucone isoflavone enriched vegetable protein whey comprising:

(a) obtaining a vegetable protein whey comprising glucone isoflavones and sufficient residual enzyme which is at least one of beta-glucosidase enzyme and esterase enzyme, and (b) reacting said glucone isoflavones with said enzyme for a time period, temperature, and pH sufficient to convert at least a majority of said glucone isoflavones in said whey to aglucone isoflavones, and thereby produce an aglucone isoflavone enriched whey.

21. The process as set forth in claim 20 wherein said time period is from about 2 hours to about 48 hours.

22. The process as set forth in claim 21 wherein said time period is about 24 hours.

23. The process as set forth in claim 20 wherein said temperature is about 40° C. to about 60° C.

24. The process as set forth in claim 23 wherein said temperature is about 60° C.

25. The process as set forth in claim 20 wherein said pH is from about 4 to about 8.

26. The process as set forth in claim 25 wherein said pH is about 4.5.

27. The process as set forth in claim 20 wherein said time period is about 24 hours, temperature is about 60° C., and pH is about 4.5.

28. The process as set forth in claim 20 further comprising:

(c) recovering a protein material from said whey to provide an aglucone isoflavone enriched whey protein.

29. The process as set forth in claim 28 wherein said whey protein comprises soybean whey.

30. The process of claim 28 wherein said whey protein is recovered by ultrafiltration.

31. The process as set forth in claim 28 wherein said whey protein is recovered by a process which comprises heating said whey at a pH, time and temperature sufficient to insolubilize said protein and thereafter separating said insolubilized protein from said whey.

32. The process as set forth in claim 31 wherein said pH is about 1 to about 2.

33. The process as set forth in claim 31 wherein said temperature is at least about 80° C. for at least about 30 minutes.

34. The process of claim 31 wherein said insolubilized protein is separated from said whey by centrifugation.

35. The process as set forth in claim 31 wherein said insolubilized protein is dewatered.

36. The aglucone isoflavone enriched whey produced by the process of claim 20.

37. The aglucone isoflavone enriched whey protein produced by the process of claim 28.

38. The process as set forth in claim 20 wherein substantially all glucone isoflavones are converted to aglucone isoflavones.

39. A process for producing an aglucone isoflavone enriched vegetable protein whey comprising:

(a) obtaining a vegetable protein whey comprising glucone isoflavones;

(b) adding supplemental enzyme which is at least one of beta-glucosidase enzyme and esterase enzyme to said whey so that the total concentration of enzyme in said whey is sufficient to convert at least a majority of glucone isoflavones in said whey to aglucone isoflavones; and (c) reacting said glucone isoflavones with said enzyme for a time period, temperature, and pH sufficient to convert at least a majority of said glucone isoflavones in said whey to aglucone isoflavones, and thereby produce an aglucone isoflavone enriched whey.

40. The process as set forth in claim 39 wherein said time period is from about 2 hours to about 48 hours.

41. The process as set forth in claim 40 wherein said time period is about 24 hours.

42. The process as set forth in claim 39 wherein said temperature is about 40° C. to about 60° C.

43. The process as set forth in claim 42 wherein said temperature is about 60° C.

44. The process as set forth in claim 39 wherein said pH is from about 4 to about 8.

45. The process as set forth in claim 44 wherein said pH is about 4.5.

46. The process as set forth in claim 39 wherein said time period is about 24 hours, said temperature is about 60° C., and said pH is about 4.5.

47. The process as set forth in claim 39 further comprising:

(d) recovering a protein material from said whey to provide an aglucone isoflavone enriched whey protein.

48. The process as set forth in claim 47 wherein said whey protein comprises soybean whey.

49. The process as set forth in claim 47 wherein said protein material is recovered by ultrafiltration.

50. The process as set forth in claim 47 wherein said protein material is recovered by a process which comprises heating said whey at a pH, time, and temperature sufficient to insolubilize said protein material and thereafter separating insolubilized protein from said whey.

51. The process as set forth in claim 50 wherein said pH is about 1 to about 2.

52. The process as set forth in claim 50 wherein said temperature is at least about 80° C. for at least about 30 minutes.

53. The process as set forth in claim 50 wherein said insolubilized protein is separated from said whey by centrifugation.

54. The process as set forth in claim 50 wherein said insolubilized protein is dewatered.

55. The aglucone isoflavone enriched whey produced by the process of claim 39.

56. The aglucone isoflavone enriched whey protein produced from the process as set forth in claim 47.

57. The process as set forth in claim 39 wherein substantially all glucone isoflavones are converted to aglucone isoflavones.

58. A process for producing an aglucone isoflavone enriched vegetable protein whey comprising:

(a) obtaining a vegetable protein whey comprising glucone isoflavones; and (b) reacting said glucone isoflavones with a sufficient amount of acid at a pH, time, and temperature sufficient to convert at least a majority of said glucone isoflavones in said whey to aglucone isoflavones, and thereby produce an aglucone isoflavone enriched whey.

59. The process as set forth in claim 58, wherein said pH is from about 1 to about 2.

60. The process as set forth in claim 59 wherein said temperature is from about 80° C. to about 90° C.

61. The process as set forth in claim 59 wherein said time is from about 30 minutes to about 180 minutes.

62. The process as set forth in claim 58 wherein said pH is about 4.5.

63. The process as set forth in claim 62 wherein said time is about 24 hours.

64. The process as set forth in claim 62 wherein said temperature is about 50° C.

65. An aglucone isoflavone enriched vegetable whey protein having a dry basis genistein content of about 2.6 to about 8.7 mg/gram and a dry basis daidzein content of about 2.5 to about 6.0 mg/gram.

66. The process as set forth in claim 1 wherein said pH is at a value at which said enzyme is most active prior to reaction with said glucone isoflavones.

67. The process as set forth in claim 20 wherein said pH is at a value at which said enzyme is most active prior to reaction with said glucone isoflavones.

68. The process as set forth in claim 39 wherein said pH is at a value at which said enzyme is most active prior to reaction with said glucone isoflavones.

69. A process for recovering in a whey protein at least 50% of an isoflavone from a vegetable protein material, comprising:

(a) obtaining a vegetable protein whey comprising isoflavones;

(b) reacting said isoflavones with a sufficient mount of an enzyme for a time period, temperature, and pH sufficient to convert at least a majority of said isoflavones in said vegetable protein whey to less soluble isoflavones, and thereby produce an isoflavone enriched whey; and (c) recovering a whey protein from said isoflavone enriched whey to provide a whey protein containing at least 50% of the isoflavones contained in said vegetable protein whey.

70. The process as set forth in claim 69 wherein said whey protein contains at least 65% of the isoflavones contained in said vegetable protein whey.

71. The process as set forth in claim 69 wherein said whey protein contains at least 80% of the isoflavones contained in said vegetable protein whey.

72. The whey protein of claim 69.

73. The whey protein of claim 70.

74. The whey protein of claim 71.

75. The process as set forth in claim 69 wherein said vegetable protein material comprises a soybean material.

76. The process as set forth in claim 69 wherein said enzyme is selected from the group consisting of beta-glucosidase enzyme and esterase enzyme.

* * * * *